US009834624B2

(12) United States Patent
Mamedov et al.

(10) Patent No.: US 9,834,624 B2
(45) Date of Patent: Dec. 5, 2017

(54) SYSTEM AND PROCESS FOR PRODUCING POLYETHYLENE

(71) Applicant: SAUDI BASIC INDUSTRIES CORPORATION, Riyadh (SA)

(72) Inventors: Aghaddin Mamedov, Sugar Land, TX (US); Mohamed Sabri Abdelghani, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 15/027,587

(22) PCT Filed: Oct. 7, 2014

(86) PCT No.: PCT/US2014/059420
§ 371 (c)(1),
(2) Date: Apr. 6, 2016

(87) PCT Pub. No.: WO2015/054196
PCT Pub. Date: Apr. 16, 2015

(65) Prior Publication Data
US 2016/0244536 A1    Aug. 25, 2016

Related U.S. Application Data

(60) Provisional application No. 61/889,660, filed on Oct. 11, 2013, provisional application No. 61/895,081, filed on Oct. 24, 2013.

(51) Int. Cl.
*C08F 10/02* (2006.01)
*C07C 2/78* (2006.01)
(Continued)

(52) U.S. Cl.
CPC .............. *C08F 10/02* (2013.01); *B01J 8/1818* (2013.01); *B01J 19/245* (2013.01); *C07C 2/78* (2013.01); *C07C 2/84* (2013.01); *C07C 5/48* (2013.01)

(58) Field of Classification Search
CPC .. C07C 2/78; C07C 11/04; C08F 10/02; B01J 19/245
(Continued)

(56) References Cited

U.S. PATENT DOCUMENTS 4,929,797 A    5/1990   Yamaguchi et al.
2003/0045761 A1*  3/2003   Kuechler ............... B01J 8/1809
                                                    585/327
(Continued)

OTHER PUBLICATIONS

Zhang et al., "Natural Gas Direct Conversion of Methane to Ethylene and Ethane" Natural Gas Chemical Industry, 1998, vol. 23, 12 pages, with translation.
(Continued)

*Primary Examiner* — Fred M Teskin
(74) *Attorney, Agent, or Firm* — Cantor Colburn LLP

(57) ABSTRACT

Systems and processes for generating polyethylene are provided. A process includes performing a first reaction with methane and oxygen to produce a first product; performing a second reaction with the first product to produce a second product; separating components from the second product; returning ethane from the second product and performing a reaction simultaneous to the first reaction; performing a third reaction to produce a third product including polyethylene and vented methane; and returning the vented methane to a feed to the first reaction.

20 Claims, 2 Drawing Sheets

(51) Int. Cl.
*C07C 2/84* (2006.01)
*C07C 5/48* (2006.01)
*B01J 8/18* (2006.01)
*B01J 19/24* (2006.01)
B01J 21/06 (2006.01)
B01J 21/10 (2006.01)

(58) Field of Classification Search
USPC .................................. 526/75; 585/315, 330
See application file for complete search history.

(56) References Cited

U.S. PATENT DOCUMENTS

| | | |
|---|---|---|
| 2006/0276679 A1 | 12/2006 | Little et al. |
| 2012/0065412 A1 | 3/2012 | Abdallah et al. |
| 2013/0317270 A1* | 11/2013 | Vanderbilt .............. C08F 10/00 585/330 |

OTHER PUBLICATIONS

International Search Report for International Application No. PCT/US2014/059420; International Filing Date: Oct. 7, 2014; dated Dec. 9, 2014; 4 Pages.

Menshchikov V A: "High purity ethylene prepn. by catalytic dimerisation of methane—removal of carbon dioxide and water and a contaminant mixt. contg. methane, rectification and pyrolysis of the sepd. ethane" Abstract only; 1 page.

Written Opinion of the International Searching Authority for International Application No. PCT/US2014/059420; International Filing Date: Oct. 7, 2014; dated Dec. 9, 2014; 6 Pages.

* cited by examiner

SYSTEM AND PROCESS FOR PRODUCING POLYETHYLENE

CROSS REFERENCE TO RELATED APPLICATIONS

This application is a 371 of International Application No. PCT/US2014/059420, filed Oct. 7, 2014, which claims priority to U.S. Application No. 61/889,660, filed Oct. 11, 2013 and U.S. Application No. 61/895,081, filed Oct. 24, 2013, all of which are incorporated herein by reference in their entirety.

TECHNICAL FIELD

The presently disclosed subject matter relates to systems and processes for producing polyethylene from methane.

BACKGROUND

Polyethylene is an important industrial polymer commonly used in packaging. One method for producing polyethylene is through methane oxidative coupling. During this process, methane can be separated from ethylene in the gas phase; however, this separation is a high energy consuming process requiring cryogenic cooling and compression-decompression cycles to achieve the necessary separation conditions of high pressure and low temperature. Further, methane oxidative coupling can have a relatively low methane conversion, rendering the process uneconomical.

Thus, there remains a need in the art for techniques for producing polyethylene that does not require the costly separation of unreacted methane from ethylene.

SUMMARY OF THE DISCLOSED SUBJECT MATTER

The presently disclosed subject matter provides systems and processes for producing polyethylene from methane. In one embodiment, a disclosed exemplary process provides for receiving a first feed including methane and oxygen. A first reaction is performed in the presence of a first oxidation catalyst to produce a first product including methane, ethylene, hydrogen, ethane, propane, propylene, carbon monoxide, carbon dioxide, and water. A second reaction is performed in the presence of a second catalyst to produce a second product including methane, ethylene, ethane, propane, propylene, carbon dioxide, and water. Substantially all of the ethane, propane, propylene, carbon dioxide, and water is separated from the second product. A second feed comprising ethane separated from the second product and oxygen is received and a reaction simultaneous to the first reaction is performed. A third reaction is performed to produce a third product including polyethylene and vented methane. Vented methane is returned to the first feed.

In accordance with another embodiment of the disclosed subject matter, systems for producing polyethylene are provided. In one embodiment, a disclosed exemplary system includes an inlet line to feed a first reactor. The first reactor, coupled to the inlet line, is configured to perform a reaction in the presence of a first oxidation catalyst to produce a first product including methane, ethylene, hydrogen, ethane, propane, propylene, carbon monoxide, carbon dioxide, and water. The system also includes a first feed line, coupled to the first reactor, to feed the first product. A second reactor, coupled to the first feed line, is configured to perform a reaction in the presence of a second catalyst to produce a second product including methane, ethylene, ethane, propane, propylene, carbon dioxide, and water. The system also includes an outlet line to separate off ethane, propane, propylene, carbon dioxide, and water from the second product. The system further includes a second feed line to feed ethane separated from the second product and oxygen to the first reactor. The system further includes a third feed line to feed methane and ethylene from the second product to the third reactor. A third reactor, coupled to the third feed line, is configured to perform a reaction to produce a third product including polyethylene. The system also includes a second outlet line, coupled to the third reactor, to allow methane to vent from the third reactor. The second outlet line is configured to return methane vented from the third reactor to the first feed.

These and other features and characteristics are more particularly described below.

DETAILED DESCRIPTION

Figure 1:
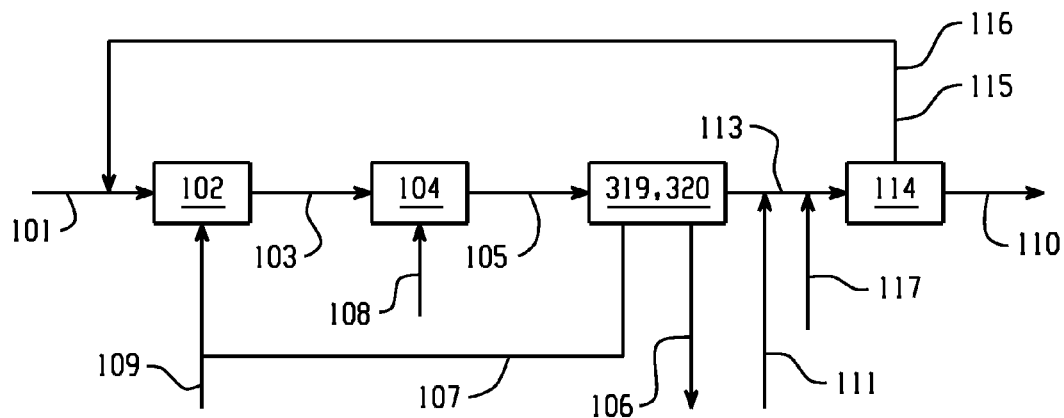
FIG. 1 is a schematic diagram depicting an exemplary process for producing polyethylene in accordance with one nonlimiting exemplary embodiment of the disclosed subject matter.
Figure 3:
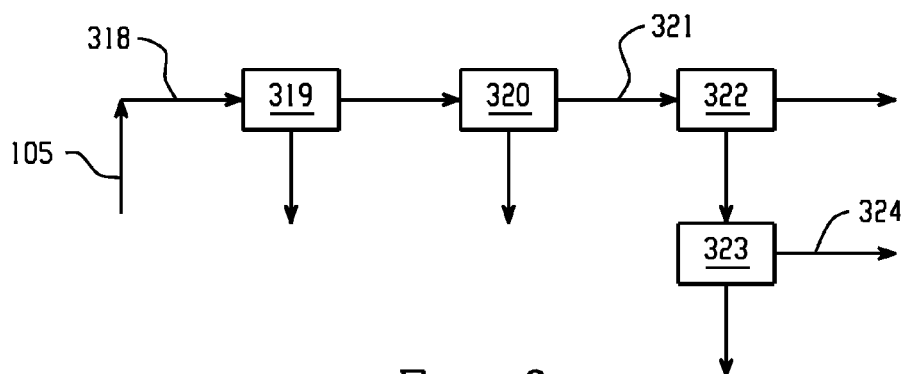
FIG. 3 is a schematic diagram depicting a process for separating off ethane, propane, propylene, carbon dioxide, and water in accordance with one nonlimiting exemplary embodiment of the disclosed subject matter.

The presently disclosed subject matter provides systems and processes for generating polyethylene from methane using an integrated process. For the purpose of illustration and not limitation, FIG. 1 is a schematic representation of an exemplary multi-stage process for the production of polyethylene according to an embodiment of the disclosed subject matter, and FIG. 3 is a schematic representation of a process for separating off ethane, propane, propylene, carbon dioxide, and water according to an embodiment of the disclosed subject matter. The process includes feeding a first feed 101, as shown in FIG. 1, including methane and oxygen into a first reactor, 102. The ratio of methane to oxygen in the first feed 101 can be about 2:1 to about 5:1. The space velocity of the first feed 101 can have a range of about 3,600 inverse hours ($h^{-1}$) to about 36,000 $h^{-1}$. The first feed 101 can be fed at atmospheric pressure. In one embodiment, a methane feed after separation from natural gas is mixed with an oxygen feed separated from air. Separation of methane from natural gas and separation of oxygen from air can be performed using any known methods. The first feed 101 can be introduced into the first reactor 102 using any suitable means known to one of ordinary skill in the art. The first reactor 102 can be any suitable reactor such as fixed bed, fluidized bed, or moving bed reactors, including an adiabatic fixed bed reactor.

The process also includes performing a reaction in the first reactor 102 in the presence of a first oxidation catalyst to produce a first product including methane, ethylene, hydrogen, ethane, propane, propylene, carbon monoxide, carbon dioxide, and water. The reaction in the first reactor 102 can be a methane oxidative coupling and can be performed at a temperature of about 700° C. to about 950° C. For example, the reaction in the first reactor 102 can be performed at a temperature of about 800° C. to about 850° C. In one embodiment, the first oxidation catalyst includes a sodium-manganese oxide-based mixed silicon dioxide compound although any suitable catalyst known in the art can be used such as a $Sr/La_2O_3$ catalyst.

The process also includes feeding the first product 103 and oxygen 108, as shown in FIG. 1, to a second reactor 104 and performing a reaction in the second reactor 104 in the presence of a second catalyst to produce a second product 105 including methane, ethylene, ethane, propane, propylene, carbon dioxide, and water. The reaction in the second reactor 104 can be performed at a temperature of about 100° C. to about 200° C. The second reactor can be any suitable reactor, such as a fixed bed reactor, which can operate at temperatures of about 180° C. to about 200° C. The contact time can be about 0.5 to about 1 second with a feed ratio of the first product 103 to oxygen 108 of about 4:1 to about 4.5:1. The reaction in the second reactor 104 can remove carbon monoxide, which can be unfavorable for the reaction in the third reactor 114, from the first product. This also reduces the energy consumption and capital cost of distillation to remove carbon monoxide from methane/ethylene product downstream. For example, the reaction in the second reactor can convert carbon monoxide and hydrogen, existing in the first product 103, to carbon dioxide and water. In one embodiment, the second catalyst includes a noble metal-based compound although any suitable catalyst known in the art can be used such as one or more catalysts selected from group consisting of $Pt/Al_2O_3$, CuO/MgO, $Pt/TiO_2$, and $CuO/TiO_2$.

The process also includes separating off ethane, propane, propylene, carbon dioxide, and water from the second product 105, as shown in FIG. 1 via outlet line 106, which can be at atmospheric pressure. While shown as one outlet line 106 for the sake of brevity, the system can include a plurality of outlet lines. For example, separate outlet lines can be used for 1) water, 2) carbon dioxide, and 3) propane and propylene as outlets from the various separation units, as shown in FIG. 3 in separation units 319 and 320. The second product 105 can be first fed 318, as shown in FIG. 3, to water and carbon dioxide separation units 319 and 320, respectively and then fed 321 to an ethane, propane, and propylene separation unit 322. For example, the water and carbon dioxide separation units can include any known methods of separation. For example carbon dioxide can be removed using an amine method, and water can be removed by cooling and compressing the reaction products to the room temperature at about 2 MegaPascals (MPa) (20 bars) followed use of a dryer. The ethane, propane, and propylene separation unit 322 can include a distillation column and ethylene/propylene refrigeration box. The process can also include an ethane separation unit 323 for separating ethane to be returned to the first reactor 102 as described in more detail below and sending C3+ to a separation train 324.

The process also includes feeding ethane 107 separated from the second product 105 and oxygen 109 to the down part of the first reactor 102. In one embodiment, the first reactor 102 can be a fixed bed reactor that can be configured to inject the addition ethane feed 107 and oxygen 109 to a lower portion of the reactor. As such, after conversion of methane and formation of products in the top portion of the first reactor 102, the ethane feed 107 and oxygen 109 can be added to convert most of the ethane in the lower portion of the first reactor 102 to ethylene. Alternatively, the first reactor 102 can include a first bed for the conversion of methane from feed 101 and a second bed for the conversion of ethane. These configurations allow for simultaneous utilization of ethane and an increase of ethylene concentration in the first product 103 of reactor 102.

Figure 4:
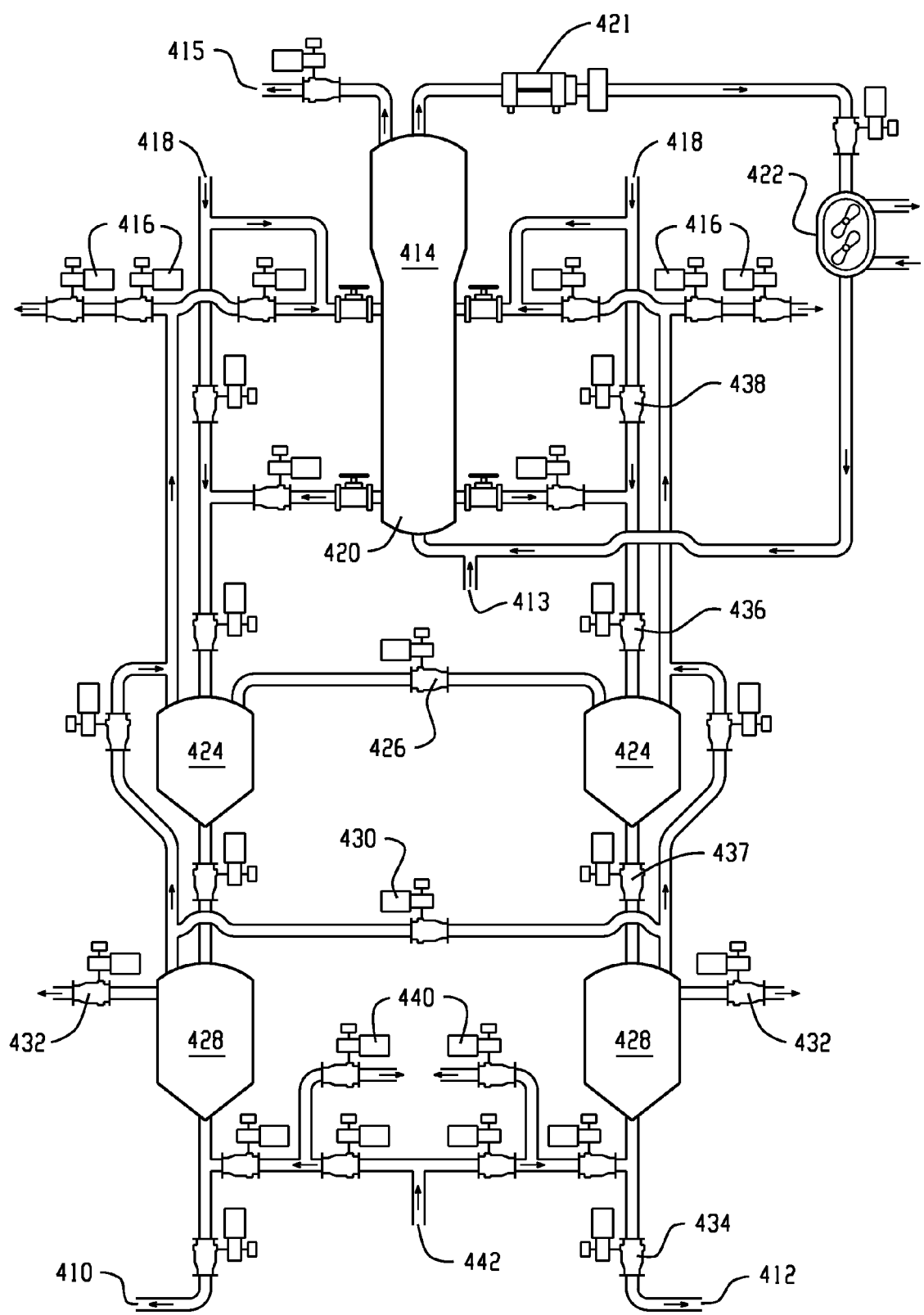
FIG. 4 is a schematic diagram of a gas phase fluidized bed reactor.

The process also includes feeding methane and ethylene 113 from the second product, as shown in FIG. 1, to a third reactor 114, performing a reaction in the third reactor 114 to produce a third product 110 including polyethylene thereby allowing methane to vent 115 from the third reactor 114, and returning the methane 116 vented from the third reactor 114 to the first feed 101. The reaction performed in the third reactor 114 can be a polymerization reaction. The third reactor 114 can be a gas phase fluidized bed reactor 414, as shown in FIG. 4 for the purpose of illustration and not limitation, to which the methane and ethylene from the second product is fed 413. This reduces the energy consumption and capital cost of distillation in separating methane and ethylene as separate products. In the reactor, gaseous monomers, co-monomers and catalyst can combine to produce a dry co-monomers resin. The resin, along with unspent catalyst and possibly polymer sheets and chunks can flow from the reactor bottom 420 to a product discharge system under its weight. The product discharge system can include a product blow tank 428, a product chamber 424 as well as various valves and piping for product conveyance, isolation, gas venting and recycling, and cross-tying with other product discharge members. For example, the other components can include a product chamber vent valve 416, purge line 418, compressor 421, cooler 422, with cooling water flowing therethrough, product chamber cross-tie valve 426, product blow tank cross-tie valve 430, product blow tank vent valve 432, product blow tank outlet valve 434, product chamber resin inlet valve 436, product purge valve 438, flare 440, product chamber outlet valve 437, and conveying gas 442. Unreacted gas (e.g. primarily methane and some ethylene) can be separated from the product 410 and returned to the reactor 414 to circulate around the reactor 414 by a compressor 421. The vent gas (e.g. methane) which is depleted from ethylene can leave the third reactor 414 from the overhead vent unit 415 and can be recycled back to the MOC reactor (as shown as 116 in FIG. 1). Byproducts from purging can sent to the purge bin via byproducts purge line 412. In one embodiment, methane is vented 415 from the third reactor 414 without exerting energy. The third reactor 414 pressure can be about 2 MPa (20 bars) and temperature can be about 100 to about 110° C. for high density polyethylene (HDPE) or about 87° C. for linear low density polyethylene (LLDPE)).

The process can also include feeding a co-monomer 117 with the methane and ethylene fed from the second product 113 to the third reactor 114. For example, the co-monomer 117 can include a 1-hexene based compound. In one embodiment, the methane and ethylene fed from the second product 113 to the third reactor 114 can include about 80% methane and about 20% ethylene by weight. Alternatively, by feeding ethylene from outside the process to the third reactor 114, the methane to ethylene ratio can be varied between about 4:1 to about 1:9. In one embodiment, the methane and ethylene can include about 10% to about 20% methane and about 80% to about 90% ethylene by weight. Furthermore, the feed can include about 0.12 mol % of hydrogen to ethylene, which can be adjusted upstream of the reactor by injecting hydrogen 111 from outside the process. Methane from the second product 105 can remain inert during the reaction in the third reactor 114.

In certain embodiments, the polyethylene product 110 can include a high-density polyethylene based compound. Methane in the third reactor 114 can limit the solubility of the co-monomer to provide the high-density polyethylene based compound.

In certain embodiments, the process does not include ethane steam cracking, which can prevent feeding a large amount of hydrogen into the third reactor 114. Not including ethane steam cracking can save on energy consumption and capital expenditure.

Figure 2:
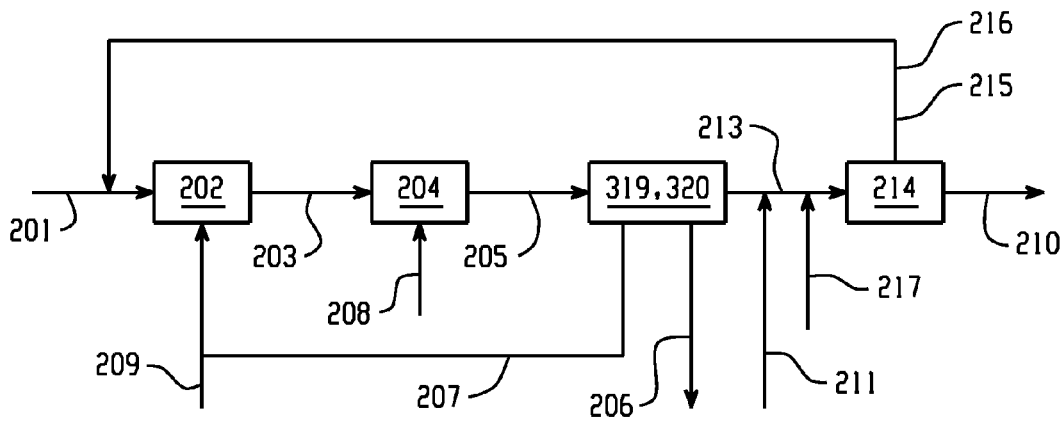
FIG. 2 shows an exemplary system for producing polyethylene in accordance with one nonlimiting exemplary embodiment of the disclosed subject matter.

For the purpose of illustration and not limitation, FIG. 2 shows a system for generating polyethylene in accordance with one exemplary embodiment of the disclosed subject matter. The system can include any of the features described above for the process for the production of polyethylene. The system includes an inlet line 201 to feed a first reactor 202. The first reactor 202 can be any suitable configuration for performing a reaction in the presence of a first oxidation catalyst to produce a first product including methane, ethylene, hydrogen, ethane, propane, propylene, carbon monoxide, carbon dioxide, and water. For example, the first reactor can have any configuration and include any of the features of the first reactor 102 described for the method above, and the first reactor 202 can be sufficient for the large-scale generation of the first product.

The system also includes a first feed line 203 to feed the first product to a second reactor 204. The second reactor 204 can be any suitable configuration for performing a reaction in the presence of a second catalyst to produce a second product 205 including methane, ethylene, ethane, propane, propylene, carbon dioxide, and water. For example, the second reactor 204 can have any configuration and include any of the features of the second reactor 104 described for the method above, and the second reactor 204 can be sufficient for the large-scale generation of the second product 205.

The system includes an outlet line 206 to separate off ethane, propane, propylene, carbon dioxide, and water from the second product, which can be at atmospheric pressure. While shown as one outlet line 206 for the sake of brevity, the system can include a plurality of outlet lines. For example, separate outlet lines can be used for 1) water, 2) carbon dioxide, and 3) propane and propylene as outlets from the various separation units, as shown in FIG. 3.

The system also includes a second feed line 207 to feed ethane separated from the second product and oxygen 209 to the down part of the first reactor 202. The configuration the first reactor 202 can include any of the features of the first reactor 102 described for the method above to allow for the injection of the addition feed 207 and oxygen 209 to the down part of the reactor 202.

The system also includes a third feed line 213 to feed methane and ethylene from the second product 205 to a third reactor 214. The third reactor 214 can be any suitable configuration for performing a reaction to produce a third product 210 including polyethylene. For example, the third reactor 214 can have any configuration and include any of the features of the third reactor 114 described for the method above, and the third reactor 214 can be sufficient for the large-scale generation of the third product. The system includes a second outlet line 215 to allow methane to vent from the third reactor 214. The system also includes a feed line 216 to return methane vented from the third reactor 214 to the first feed 201. In one embodiment, the system includes separation units 319, 320 to separate off ethane, propane, propylene, carbon dioxide, and water from the second product, for example as described above for the process of producing polyethylene and as shown in FIG. 3. For example, the separation units can be a distillation column and can include ethylene/propylene refrigeration cold box. In another embodiment, the third reactor 214 includes a venting unit. The system can also include a feed line 217 to feed a co-monomer with the methane and ethylene fed from the second product 205 to the third reactor 214. Furthermore, the system for producing polyethylene can include any of the features described herein above for the process for producing polyethylene. For example, the co-monomer can include a 1-hexene based compound. In one embodiment, the methane and ethylene fed from the second product 205 to the third reactor 214 can include about 80% methane and about 20% ethylene by weight. Alternatively, by feeding ethylene from outside the process to the third reactor 214, the methane to ethylene ratio can be varied between about 4:1 to about 1:9. In one embodiment, the methane and ethylene can include about 10% to about 20% methane and about 80% to about 90% ethylene by weight. Furthermore, the feed can include about 0.12 mol % of hydrogen to ethylene, which can be adjusted upstream of the reactor by injecting hydrogen 211 from outside the process.

The following example is merely illustrative of the process disclosed herein and is not intended to limit the scope hereof.

EXAMPLE

For the purpose of illustration and not limitation, a reaction can be performed for the first reactor as follows: 7 grams (g) of a sodium manganese catalyst can be loaded into a U-type quartz reactor with inside diameter (I.D.) of 10 millimeters (mm). A methane and oxygen mixture with a ratio of 3:1 and total flow rate 14 milliliters per second (ml/sec) can be fed from the top of the U-type reactor and an ethane oxygen mixture with a ratio of 3:1 and flow rate 14 cubic centimeters per second (cc/sec) can be fed to the bottom of the reactor. The U-type quartz reactor can be located inside an electrically-heated furnace at 850° C. and the products of the reaction can be removed through the other exit of the U type of the reactor for analysis. The reaction can also be carried out using other methane oxidative coupling catalyst such as $Sr/La_2O_3$ using different reaction conditions, such as a catalyst loading of 7 milliliters (ml) and methane oxygen mixture flow rate of 7 cc/min at 800° C.

For the purpose of illustration and not limitation, a reaction can be performed for the second reactor using the same process described above for the first reactor but using a different reaction temperature, feed composition and catalysts. For example, the reaction can be performed for the second reactor as described above for the first reactor with the following changes: 7 g of a catalyst selected from group of catalysts including $Pt/Al_2O_3$, CuO/MgO, $Pt/TiO_2$, and $CuO/TiO_2$ can be loaded into the quartz reactor with an I.D. of 10 mm. The outlet of the first reactor and oxygen can be fed with a flow rate 3 cc/min to the tubular quartz reactor. The reaction temperature can be 200° C.

In certain embodiments of the disclosed subject matter, the performing a first, second, and third reactions takes place in different reaction chambers. In certain embodiments of the disclosed subject matter, the performing a first reaction includes maintaining a temperature of about 700° C. to about 950° C. For example, the performing a first reaction can include maintaining a temperature of about 800° C. to about 850° C. The first oxidation catalyst can include a sodium-manganese oxide-based mixed silicon dioxide compound. In certain embodiments of the disclosed subject matter, the performing a second reaction includes maintaining a temperature of about 100° C. to about 200° C. The second reaction can remove carbon monoxide from the first product. The second catalyst can include a noble metal-based compound.

In certain embodiments of the disclosed subject matter, the process includes substantially separating water and carbon dioxide from the second product to create a second product intermediary, and then separating ethane, propane, and propylene from the second product intermediary. In certain embodiments of the disclosed subject matter, the first reaction includes methane oxidative coupling. The reaction simultaneous to the first reaction can include oxidative dehydrogenation of ethane. The first reaction can take place in a first reactor and second feed comprising ethane separated from the second product and oxygen can be fed to a lower portion of the first reactor. The oxidative dehydrogenation of ethane can take place in the lower portion of the first reactor. In certain embodiments, the first reaction takes place in a first reactor at a first set of conditions and the oxidative dehydrogenation of ethane takes place in the first reactor at the same first set of conditions. The first oxidation catalyst can be modified by elements including potassium, tin, cerium, and tungsten.

In certain embodiments of the disclosed subject matter, the process includes feeding a co-monomer to the third reaction. For example, the co-monomer can include a 1-hexene based compound. The process can include feeding hydrogen to the third reaction. The methane and ethylene fed from the second product to the third reaction can include about 80% to about 10% methane and about 20% to about 90% ethylene by weight. The performing a third reaction can include maintaining a temperature of about 100° C. and/or a pressure of about 2 MPa (20 bars).

In certain embodiments of the disclosed subject matter, the polyethylene includes a high-density polyethylene based compound. Methane in the third reaction can limit the solubility of the co-monomer to provide the high-density polyethylene based compound. In certain embodiments of the disclosed subject matter, the system includes separation units, coupled to the outlet line, to separate off ethane, propane, propylene, carbon dioxide, and water from the second product. For example, the separation units can include ethylene and propylene refrigeration cold box. In certain embodiments of the disclosed subject matter, the third reactor includes a venting unit. The system can include a fourth feed line, coupled to the third feed line, to feed a co-monomer to the third reactor. The second feed line can be coupled to a lower portion of the first reactor.

The processes and systems disclosed herein include at least the following embodiments:

Embodiment 1

A process for producing polyethylene from methane, comprising: receiving a first feed comprising methane and oxygen; performing a first reaction in the presence of a first oxidation catalyst to produce a first product comprising methane, ethylene, hydrogen, ethane, propane, propylene, carbon monoxide, carbon dioxide, and water; performing a second reaction in the presence of a second catalyst to produce a second product comprising methane, ethylene, ethane, propane, propylene, carbon dioxide, and water; separating off ethane, propane, propylene, carbon dioxide, and water from the second product; receiving a second feed comprising ethane separated from the second product and oxygen and performing a reaction simultaneous to the first reaction; performing a third reaction to produce a third product comprising polyethylene and vented methane; and returning the vented methane to the first feed.

Embodiment 2

The process of Embodiment 1, wherein the performing a first, second, and third reactions takes place in different reaction chambers.

Embodiment 3

The process of Embodiment 1 or Embodiment 2, wherein the performing a first reaction comprises maintaining a temperature of about 700° C. to about 950° C.

Embodiment 4

The process of Embodiment 3, wherein the performing a first reaction comprises maintaining a temperature of about 800° C. to about 850° C.

Embodiment 5

The process of any of Embodiments 1-4, wherein the first oxidation catalyst comprises a sodium-manganese oxide-based mixed silicon dioxide compound.

Embodiment 6

The process of any of Embodiments 1-5, wherein the performing a second reaction comprises maintaining a temperature of about 100° C. to about 200° C.

Embodiment 7

The process of any of Embodiments 1-6, wherein the performing a second reaction comprises removing carbon monoxide from the first product.

Embodiment 8

The process of any of Embodiments 1-7, wherein the second catalyst comprises a noble metal-based compound.

Embodiment 9

The process of any of Embodiments 1-8, further comprising substantially separating water and carbon dioxide from the second product to create a second product intermediary, and then separating ethane, propane, and propylene from the second product intermediary.

Embodiment 10

The process of any of Embodiments 1-9, wherein the first reaction comprises methane oxidative coupling.

Embodiment 11

The process of any of Embodiments 1-10, wherein the reaction simultaneous to the first reaction comprises oxidative dehydrogenation of ethane.

Embodiment 12

The process of any of Embodiments 1-11, wherein the first reaction takes place in a first reactor and second feed comprising ethane separated from the second product and oxygen is fed to a lower portion of the first reactor.

Embodiment 13

The process of any of Embodiments 1-12, wherein the oxidative dehydrogenation of ethane takes place in the lower portion of the first reactor.

Embodiment 14

The process of any of Embodiments 1-13, wherein the first reaction takes place in a first reactor at a first set of conditions and wherein the oxidative dehydrogenation of ethane takes place in the first reactor at the first set of conditions.

Embodiment 15

The process of any of Embodiments 1-14, wherein the first oxidation catalyst is modified by elements comprising potassium, tin, cerium, and tungsten.

Embodiment 16

The process of any of Embodiments 1-15, further comprising feeding a co-monomer to the third reaction.

Embodiment 17

The process of Embodiment 16, wherein the co-monomer comprises a 1-hexene based compound.

Embodiment 18

The process of any of Embodiments 1-17, further comprising feeding hydrogen to the third reaction.

Embodiment 19

The process of any of Embodiments 1-18, wherein methane and ethylene, fed from the second product to the third reaction, comprises about 10% to about 80% methane and about 20% to about 90% ethylene by weight.

Embodiment 20

The process of any of Embodiments 1-19, wherein the performing a third reaction comprises maintaining a temperature of about 100° C.

Embodiment 21

The process of any of Embodiments 1-20, wherein the performing a third reaction comprises maintaining a pressure of about 2 MegaPascals.

Embodiment 22

The process of any of Embodiments 1-21, wherein the polyethylene comprises a high-density polyethylene based compound.

Embodiment 23

The process of Embodiment 22, further comprising feeding a co-monomer to the third reaction, wherein the methane in the third reaction limits the solubility of the co-monomer to provide the high-density polyethylene based compound.

Embodiment 24

A system for generating polyethylene, comprising: an inlet line to feed a first reactor; a first reactor, coupled to the inlet line, configured to perform a reaction in the presence of a first oxidation catalyst to produce a first product comprising methane, ethylene, hydrogen, ethane, propane, propylene, carbon monoxide, carbon dioxide, and water; a first feed line, coupled to the first reactor, to feed the first product; a second reactor, coupled to the first feed line, configured to perform a reaction in the presence of a second catalyst to produce a second product comprising methane, ethylene, ethane, propane, propylene, carbon dioxide, and water; an outlet line to separate off ethane, propane, propylene, carbon dioxide, and water from the second product; a second feed line to feed ethane separated from the second product and oxygen to the first reactor; a third feed line to feed methane and ethylene from the second product to the third reactor; a third reactor, coupled to the third feed line, configured to perform a reaction to produce a third product comprising polyethylene; and a second outlet line, coupled to the third reactor, to allow methane to vent from the third reactor, the second outlet line configured to return methane vented from the third reactor to the first feed.

Embodiment 25

The system of Embodiment 24, further comprising separation units, coupled to the outlet line, to separate off ethane, propane, propylene, carbon dioxide, and water from the second product.

Embodiment 26

The system of Embodiment 25, wherein the separation units comprise a propylene refrigeration cold box.

Embodiment 27

The system of any of Embodiments 24-26, wherein the third reactor comprises a venting unit.

Embodiment 28

The system of any of Embodiments 24-27, further comprising a fourth feed line, coupled to the third feed line, to feed a co-monomer to the third reactor.

Embodiment 29

The system of any of Embodiments 24-28, wherein the second feed line is coupled to a lower portion of the first reactor Although the presently disclosed subject matter and its advantages have been described in detail, it should be understood that various changes, substitutions and alterations can be made herein without departing from the spirit and scope of the disclosed subject matter as defined by the appended claims. Moreover, the scope of the disclosed subject matter is not intended to be limited to the particular embodiments described in the specification. As one of ordinary skill in the art will readily appreciate from the disclosure of the disclosed subject matter, alternatives presently existing or later to be developed that perform substantially the same function or achieve substantially the same result as the corresponding embodiments described herein can be utilized according to the presently disclosed subject matter. Accordingly, the appended claims are intended to include within their scope such alternatives.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "option-ally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The disclosed subject matter is not to be limited in scope by the specific embodiments described herein. Indeed, various modifications in addition to those described herein will become apparent to those skilled in the art from the foregoing description. Such modifications are intended to fall within the scope of the appended claims.

We claim:

1. A process for producing polyethylene from methane, comprising:
   receiving a first feed comprising methane and oxygen;
   performing a first reaction in the presence of a first oxidation catalyst to produce a first product comprising methane, ethylene, hydrogen, ethane, propane, propylene, carbon monoxide, carbon dioxide, and water;
   performing a second reaction in the presence of a second catalyst to produce a second product comprising methane, ethylene, ethane, propane, propylene, carbon dioxide, and water;
   separating off ethane, propane, propylene, carbon dioxide, and water from the second product;
   receiving a second feed comprising ethane separated from the second product and oxygen and performing a reaction simultaneous to the first reaction;
   performing a third reaction to produce a third product comprising polyethylene and vented methane; and
   returning the vented methane to the first feed.

2. The process of claim 1, wherein the performing a first, second, and third reactions takes place in different reaction chambers.

3. The process of claim 1, wherein the performing a first reaction comprises maintaining a temperature of about 700° C. to about 950° C.

4. The process of claim 1, wherein the first oxidation catalyst comprises a sodium-manganese oxide-based mixed silicon dioxide compound.

5. The process of claim 1, wherein the performing a second reaction comprises maintaining a temperature of about 100° C. to about 200° C.

6. The process of claim 1, wherein the performing a second reaction comprises removing carbon monoxide from the first product.

7. The process of claim 1, further comprising substantially separating water and carbon dioxide from the second product to create a second product intermediary, and then separating ethane, propane, and propylene from the second product intermediary.

8. The process of claim 1, wherein the reaction simultaneous to the first reaction comprises oxidative dehydrogenation of ethane.

9. The process of claim 1, wherein the first reaction takes place in a first reactor and second feed comprising ethane separated from the second product and oxygen is fed to a lower portion of the first reactor.

10. The process of claim 8, wherein the first reaction takes place in a first reactor at a first set of conditions and wherein the oxidative dehydrogenation of ethane takes place in the first reactor at the first set of conditions.

11. The process of claim 1, further comprising feeding a co-monomer to the third reaction.

12. The process of claim 1, further comprising feeding hydrogen to the third reaction.

13. The process of claim 1, wherein methane and ethylene, fed from the second product to the third reaction, comprises about 10% to about 80% methane and about 20% to about 90% ethylene by weight.

14. The process of claim 1, wherein the performing a third reaction comprises maintaining a temperature of about 100° C. and a pressure of about 2 MegaPascals.

15. A system for generating polyethylene, comprising:
an inlet line to feed a first reactor;
a first reactor, coupled to the inlet line, configured to perform a reaction in the presence of a first oxidation catalyst to produce a first product comprising methane, ethylene, hydrogen, ethane, propane, propylene, carbon monoxide, carbon dioxide, and water;
a first feed line, coupled to the first reactor, to feed the first product;
a second reactor, coupled to the first feed line, configured to perform a reaction in the presence of a second catalyst to produce a second product comprising methane, ethylene, ethane, propane, propylene, carbon dioxide, and water;
an outlet line to separate off ethane, propane, propylene, carbon dioxide, and water from the second product;
a second feed line to feed ethane separated from the second product and oxygen to the first reactor;
a third reactor, configured to perform a reaction to produce a third product comprising polyethylene;
a third feed line coupled to the third reactor to feed methane and ethylene from the second product to the third reactor;
and
a second outlet line, coupled to the third reactor, to allow methane to vent from the third reactor, the second outlet line configured to return methane vented from the third reactor to the first feed.

16. The system of claim 15, further comprising separation units, coupled to the outlet line, to separate off ethane, propane, propylene, carbon dioxide, and water from the second product.

17. The system of claim 16, wherein the separation units comprise a propylene refrigeration cold box.

18. The system of claim 15, wherein the third reactor comprises a venting unit.

19. The system of claim 15, further comprising a fourth feed line, coupled to the third feed line, to feed a co-monomer to the third reactor.

20. The system of claim 15, wherein the second feed line is coupled to a lower portion of the first reactor.

* * * * *